US00PP36752P2

(12) United States Plant Patent
Hofmann

(10) Patent No.: US PP36,752 P2
(45) Date of Patent: Jun. 17, 2025

(54) ***JAMESBRITTENIA* PLANT NAMED 'INJAMLAVFL'**

(50) Latin Name: *Jamesbrittenia hybrida*
Varietal Denomination: INJAMLAVFL

(71) Applicant: Silvia Hofmann, Mainz (DE)

(72) Inventor: Silvia Hofmann, Mainz (DE)

(73) Assignee: INNOVAPLANT ZIERPFLANZEN GmbH & Co. KG, Gensingen (DE)

( * ) Notice: Subject to any disclaimer, the term of this patent is extended or adjusted under 35 U.S.C. 154(b) by 0 days.

(21) Appl. No.: 18/956,377

(22) Filed: Nov. 22, 2024

(51) Int. Cl.
*A01H 5/02* (2018.01)
*A01H 6/00* (2018.01)

(52) U.S. Cl.
USPC ..... Plt./485
CPC ..... *A01H 6/00* (2018.05)

(58) Field of Classification Search
USPC ..... Plt./485, 263.1
CPC ..... A01H 5/02
See application file for complete search history.

*Primary Examiner* — Kent L Bell
(74) *Attorney, Agent, or Firm* — C. Anne Whealy

(57) ABSTRACT

A new and distinct *Jamesbrittenia* plant named 'INJAMLAVFL', characterized by its upright to outwardly spreading and mounding plant habit; vigorous growth habit and rapid growth rate; freely branching habit; dense and bushy plant form; early and freely flowering habit; relatively large single-type flowers that are bright red in color with bright yellow green-colored centers and excellent garden performance.

2 Drawing Sheets

Figure 1:
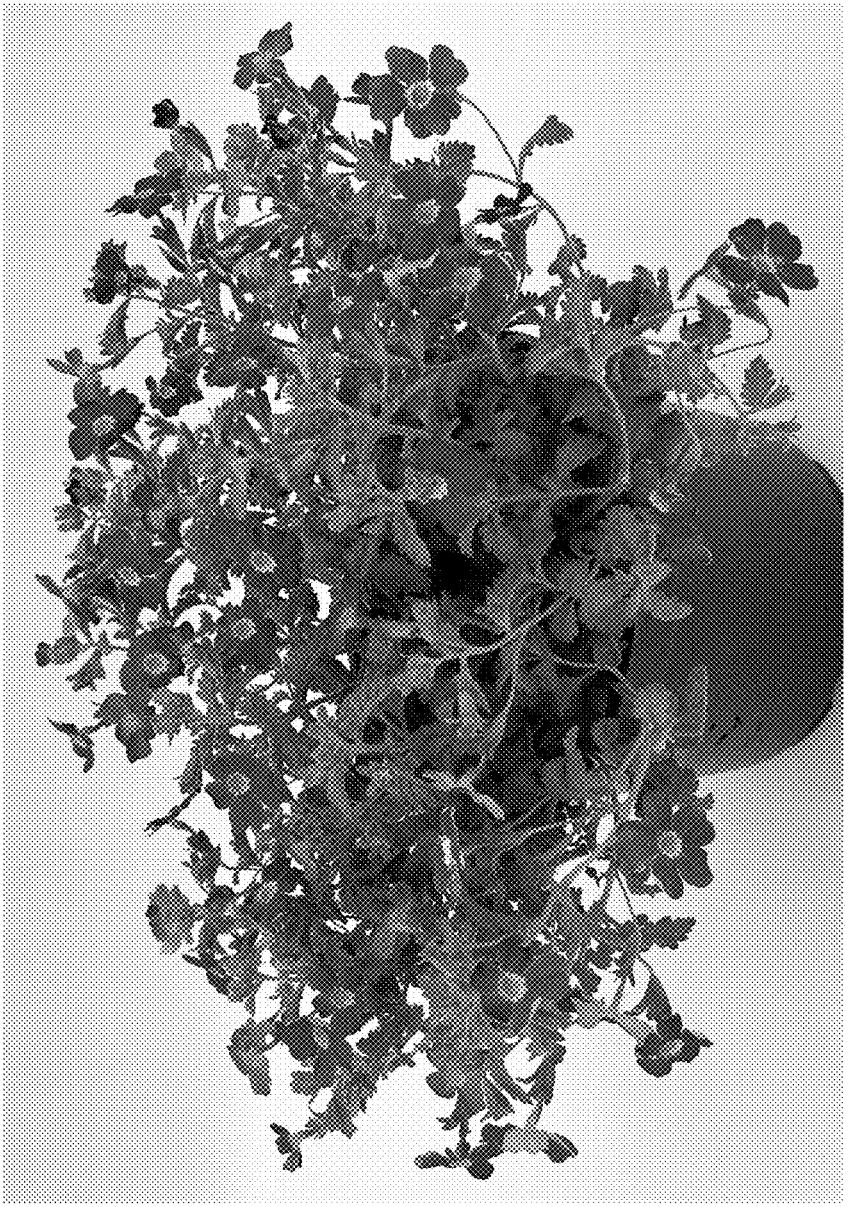

Botanical designation: *Jamesbrittenia hybrida.*
Cultivar denomination: 'INJAMLAVFL'.

BACKGROUND OF THE INVENTION

The present invention relates to a new and distinct cultivar of *Jamesbrittenia* plant, botanically known as *Jamesbrittenia hybrida*, commonly referred to as South African Phlox and hereinafter referred to by the name 'INJAMLAVFL'.

The new *Jamesbrittenia* plant is a product of a planned breeding program conducted by the Inventor in Gensingen, Germany. The objective of the breeding program is to create new compact, freely-branching and uniformly mounding *Jamesbrittenia* plants with early and freely flowering habit, large attractive flowers and good garden performance.

The new *Jamesbrittenia* plant originated from a cross-pollination made by the Inventor on Jul. 16, 2021 in Gensingen, Germany of a proprietary selection of *Jamesbrittenia hybrida* identified as code number Ja 20 3-1, not patented, as the female, or seed, parent with a proprietary selection of *Jamesbrittenia hybrida* identified as code number Ja 20 25-11, not patented, as the male, or pollen, parent. The new *Jamesbrittenia* plant was discovered and selected by the Inventor as a single flowering plant within the progeny of the stated cross-pollination in a controlled greenhouse environment in Gensingen, Germany on Apr. 3, 2022.

Asexual reproduction of the new *Jamesbrittenia* plant by vegetative terminal cuttings in a controlled greenhouse environment in Gensingen, Germany since Apr. 3, 2022 has shown that the unique features of this new *Jamesbrittenia* plant are stable and reproduced true to type in successive generations.

SUMMARY OF THE INVENTION

Plants of the new *Jamesbrittenia* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'INJAMLAVFL'. These characteristics in combination distinguish 'INJAMLAVFL' as a new and distinct *Jamesbrittenia* plant:

1. Upright to outwardly spreading and mounding plant habit.
2. Vigorous growth habit and rapid growth rate.
3. Freely branching habit; dense and bushy plant form.
4. Early and freely flowering habit.
5. Relatively large single-type flowers that are bright red in color with bright yellow green-colored centers.
6. Excellent garden performance.

Plants of the new *Jamesbrittenia* can be compared to plants of the female parent selection. In side-by-side comparisons, plants of the new *Jamesbrittenia* differ primarily from plants of the female parent selection in the following characteristics:

1. Plants of the new *Jamesbrittenia* are more freely branching than plants of the female parent selection.
2. Plants of the new *Jamesbrittenia* have larger flowers than plants of the female parent selection.
3. Flowers of plants of the new *Jamesbrittenia* are bright red in color with bright yellow green-colored centers whereas flowers of plants of the female parent selection are salmon pink in color.

Plants of the new *Jamesbrittenia* can be compared to plants of the male parent selection. In side-by-side comparisons, plants of the new *Jamesbrittenia* differ primarily from plants of the male parent selection in the following characteristics:

1. Plants of the new *Jamesbrittenia* are more vigorous and stronger than plants of the male parent selection.

2. Plants of the new *Jamesbrittenia* have larger flowers than plants of the male parent selection.

Plants of the new *Jamesbrittenia* can also be compared to plants of *Jamesbrittenia hybrida* 'Sunbrittenia Scarlet', not patented. In side-by-side comparisons, plants of the new *Jamesbrittenia* differ primarily from plants of 'Sunbrittenia Scarlet' in the following characteristics:

1. Plants of the new *Jamesbrittenia* are not as vigorous as plants of 'Sunbrittenia Scarlet'.
2. Plants of the new *Jamesbrittenia* are more freely branching than plants of 'Sunbrittenia Scarlet'.
3. Plants of the new *Jamesbrittenia* flower earlier than plants of 'Sunbrittenia Scarlet'.
4. Plants of the new *Jamesbrittenia* have shorter peduncles than plants of 'Sunbrittenia Scarlet'.

BRIEF DESCRIPTION OF THE PHOTOGRAPHS

The accompanying colored photographs illustrate the overall appearance of the new *Jamesbrittenia* plant showing the colors as true as it is reasonably possible to obtain in colored reproductions of this type. Colors in the photographs may differ slightly from the color values cited in the detailed botanical description which accurately describe the colors of the new *Jamesbrittenia* plant.

The photograph on the first sheet (FIG. 1) is a side perspective view of a typical flowering plant of 'INJAMLAVFL' grown in a container.

Figure 2:
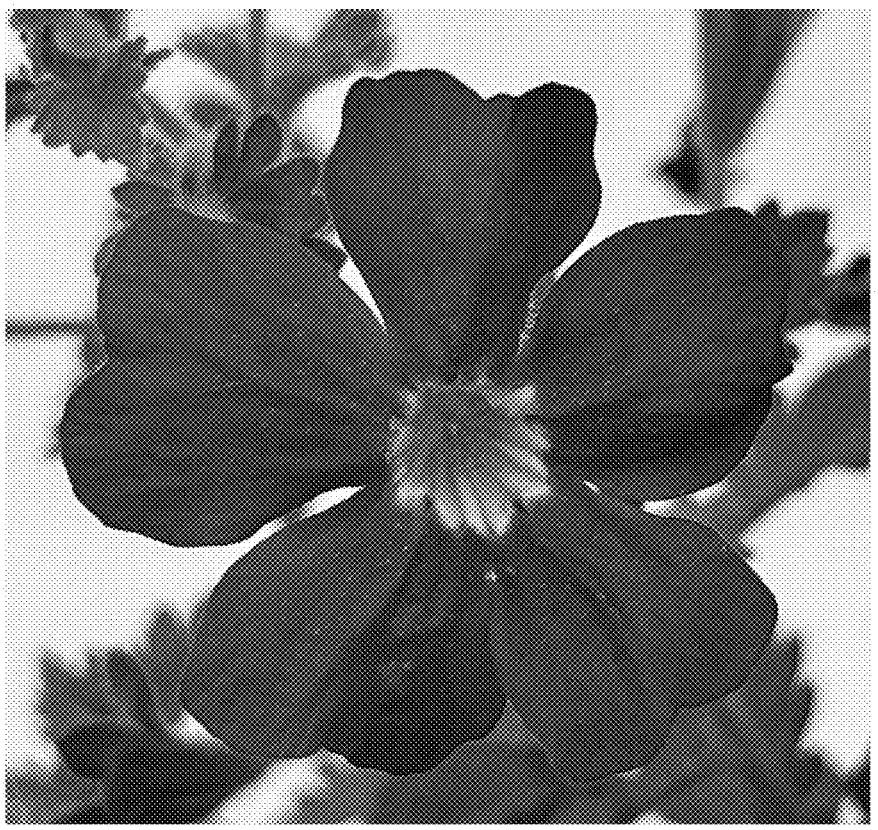

The photograph on the second sheet (FIG. 2) is a close-up view of a typical flower of 'INJAMLAVFL'.

DETAILED BOTANICAL DESCRIPTION

The aforementioned photographs and following observations and measurements describe plants grown during the late summer to early autumn in 813 ml containers in a glass-covered greenhouse in Loudon, New Hampshire and under cultural practices typical of commercial *Jamesbrittenia* production. During the production of the plants, day temperatures ranged from 18° C. to 20° C. and night temperatures ranged from 16° C. to 18° C. Plants were pinched one time and were eight weeks from planting rooted young plants when the photographs and description were taken. In the following description, color references are made to The Royal Horticultural Society Colour Chart, 2015 Edition, except where general terms of ordinary dictionary significance are used.

Botanical classification: *Jamesbrittenia hybrida* 'INJAMLAVFL'.

Parentage:

*Female, or seed, parent*.—Proprietary selection of *Jamesbrittenia hybrida* identified as code number Ja 20 3-1, not patented.

*Male, or pollen, parent*.—Proprietary selection of *Jamesbrittenia hybrida* identified as code number Ja 20 25-11, not patented.

Propagation:

*Type*.—Terminal vegetative cuttings.

*Time to initiate roots, summer*.—About 14 days at temperatures about 25° C.

*Time to initiate roots, winter*.—About 20 days at temperatures about 25° C.

*Time to produce a rooted young plant, summer*.—About 20 days at temperatures about 25° C.

*Time to produce a rooted young plant, winter*.—About 25 days at temperatures about 20° C.

*Root description*.—Fine, fibrous; typically white in color, actual color of the roots is dependent on substrate composition, water quality, fertilizer type and formulation, substrate temperature and physiological age of roots.

*Rooting habit*.—Moderately freely branching; medium density.

Plant description:

*Plant and growth habit*.—Upright to outwardly spreading and mounding plant habit; freely branching habit with lateral branches potentially developing at every node, dense and bushy plant form; pinching enhances development of lateral branches; vigorous growth habit and rapid growth rate.

*Plant height*.—About 16 cm to 18 cm.

*Plant diameter* (*area of spread*).—About 30 cm to 33 cm.

*Lateral branches*.—Length: About 20 cm to 22 cm. Diameter: About 2.5 mm. Internode length: About 1.75 cm to 2.25 cm. Strength: Strong; flexible, wiry. Aspect: Initially upright then outwardly spreading to horizontal and eventually trailing. Texture and luster: Densely pubescent; pubescence, fine; slightly glossy. Color, developing and developed: Close to 144A.

Leaf description:

*Arrangement*.—Opposite; leaves simple.

*Length*.—About 2.5 cm to 2.75 cm.

*Width*.—About 1.5 cm to 1.75 cm.

*Shape*.—Ovate with lanceolate tendencies.

*Apex*.—Acute.

*Base*.—Cuneate with truncate tendencies.

*Margin*.—Crenate to dentate with shallow to medium lobing; sinuses divergent.

*Texture and luster, upper surface*.—Mostly glabrous with pubescence towards the base; matte to slightly glossy.

*Texture and luster, lower surface*.—Mostly glabrous with pubescence along veins; matte.

*Venation pattern*.—Pinnate.

*Color*.—Developing leaves, upper surface: Close to NN137A. Developing leaves, lower surface: Close to NN137B to NN137C. Fully developed leaves, upper surface: Close to NN137A; venation, close to NN137B. Fully developed leaves, lower surface: Close to NN137C; venation, close to 144A to 144B.

*Petioles*.—Length: About 8 mm to 10 mm. Diameter: About 1.5 mm. Strength: Moderately strong, flexible. Texture and luster, upper and lower surfaces: Pubescent; matte to slightly glossy. Color, upper and lower surfaces: Close to 144A.

*Stipules*.—Quantity and arrangement: Two at petiole attachment to stem. Length: About 5 mm. Width: About 3.5 mm to 4 mm. Shape: Narrowly ovate. Color, upper surface: Close to NN137A. Color, lower surface: Close to NN137C.

Flower description:

*Flower type and flowering habit*.—Single terminal and axillary star-shaped salverform flowers; flowers face upward to slightly outwardly; freely flowering habit with flowers potentially forming at every node.

*Natural flowering season*.—Long flowering period, plants flower from early spring until the autumn, flowering continuous during this period; early flowering habit.

*Flower longevity on the plant*.—Depending on temperatures, flowers last about three to seven days; flowers persistent.

*Fragrance*.—None detected.

*Flower buds*.—Length: About 5 mm. Diameter: About 1.5 mm. Shape: Oblong. Texture and luster: Pubescent; glossy. Color: Close to 144B.

*Flower diameter*.—About 2.5 cm to 2.7 cm.

*Flower depth* (*height*).—About 2 cm to 2.2 cm.

*Throat diameter*.—About 5 mm.

*Tube length*.—About 1.75 cm to 1.8 cm.

*Tube diameter, proximally*.—About 2 mm.

*Petals*.—Quantity and arrangement: Five petals fused in a single salverform whorl. Petal lobe length (from throat): About 1.1 cm to 1.25 cm. Petal lobe width: About 1 cm to 1.1 cm. Petal lobe shape: Broadly cordate. Petal lobe apex: Truncate and retuse. Petal lobe margin: Entire; slightly undulate. Petal lobe texture and luster, upper surface: Smooth, glabrous; velvety; matte. Petal lobe texture and luster, lower surface: Smooth, glabrous; matte. Throat texture and luster: Smooth, glabrous; matte. Tube texture and luster: Densely pubescent; matte. Color: When opening, upper surface: Close to N45A; centers, close to 154A. When opening, lower surface: Close to N45B. Fully opened, upper surface: Close to 46B; centers, close to 154A to 154B; venation, similar to lamina colors; colors do not change with subsequent development. Fully opened, lower surface: Close to 56A to 56B; towards the tube, close to 154B to 154C; venation, similar to lamina colors; colors do not change with subsequent development. Flower throat (inside): Distally, close to 154A to 154B and proximally, close to 144A to 144B; venation, similar to lamina colors. Flower tube (outside): Close to 144C; venation, close to 144C.

*Sepals*.—Quantity and arrangement: Five sepals fused in a single star-shaped whorl; sepals flare outwardly. Calyx length: About 1.1 cm. Calyx diameter: About 3.5 mm. Sepal length: About 1.1 cm. Sepal width: About 1.5 mm to 2 mm. Shape: Linear. Apex: Acute. Margin: Entire. Texture and luster, upper surface: Slightly pubescent; slightly glossy. Texture and luster, lower surface: Densely pubescent; slightly glossy. Color: When opening and fully developed, upper surface: Close to 144A. When opening and fully developed, lower surface: Close to 144A.

*Peduncles*.—Length: About 1.2 cm to 1.6 cm. Width: About 1 mm. Strength: Strong; wiry and flexible. Angle: About 45° from the stem axis. Texture and luster: Pubescent; slightly glossy. Color: Close to 144A.

*Reproductive organs*.—Stamens: Quantity per flower: About five. Filament length: About 1.4 cm to 1.6 cm. Filament color: Close to 154D. Anther size: About 1 mm by 2 mm. Anther shape: Oblong. Anther color: Close to 6A to 6B. Pollen amount: None observed. Pistils: Quantity per flower: One. Pistil length: About 1.75 cm. Style length: About 1.5 cm. Style color: Close to NN155D. Stigma diameter: About 0.5 mm. Stigma shape: Tapering. Stigma color: Close to 144A. Ovary color: Close to 144A to 144B.

*Seeds and fruits*.—To date, seed and fruit development has not been observed on plants of the new *Jamesbrittenia*.

Pathogen & pest resistance: To date, plants of the new *Jamesbrittenia* have not been noted to be resistant to pathogens and pests common to *Jamesbrittenia* plants.

Garden performance: Plants of the new *Jamesbrittenia* have been observed to have excellent garden performance and have been observed to tolerate rain, wind and temperatures ranging from about 1° C. to about 35° C.

It is claimed:

1. A new and distinct *Jamesbrittenia* plant named 'INJAMLAVFL' as herein illustrated and described.

* * * * *